(12) United States Patent
Kano et al.

(10) Patent No.: US 10,660,664 B2
(45) Date of Patent: May 26, 2020

(54) SURGICAL APPARATUS

(71) Applicant: OLYMPUS CORPORATION, Tokyo (JP)

(72) Inventors: Akihito Kano, Tachikawa (JP); Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 15/259,276

(22) Filed: Sep. 8, 2016

(65) Prior Publication Data

US 2016/0374713 A1    Dec. 29, 2016

Related U.S. Application Data

(63) Continuation of application No. PCT/JP2016/064640, filed on May 17, 2016.

(30) Foreign Application Priority Data

May 27, 2015 (JP) ................................. 2015-107773

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1442* (2013.01); *A61B 18/1445* (2013.01);
(Continued)

(58) Field of Classification Search
CPC .... A61B 17/320068; A61B 17/320092; A61B 2017/320072; A61B 2017/320073;
(Continued)

(56) References Cited

U.S. PATENT DOCUMENTS 5,322,055 A    6/1994  Davison et al.
6,254,623 B1   7/2001  Haibel, Jr. et al.
(Continued)

FOREIGN PATENT DOCUMENTS

CN    101190138 A    6/2008
EP    1 875 875 A1   1/2008
(Continued)

OTHER PUBLICATIONS

International Preliminary Report on Patentability together with the Written Opinion from related International Application No. PCT/JP2016/064640 dated Dec. 7, 2017.
(Continued)

*Primary Examiner* — Tan-Uyen T Ho
*Assistant Examiner* — Chima U Igboko
(74) *Attorney, Agent, or Firm* — Scully, Scott, Murphy & Presser, P.C.

(57) ABSTRACT

A vibration transmitting member for use with a clamp member. The vibration transmitting member provided with vibration from an ultrasonic transducer and including: a body having a distal portion with a surface and an opposite surface, the body further having a proximal portion; wherein: the body extending along a longitudinal axis extending from the proximal toward the distal portion, the surface opposes the clamp member and having a ridge extending along the longitudinal axis, the ridge extends toward the clamp member in a thickness direction more than other portions of the surface, the opposite surface opposes the surface and having a projection extending along the longitudinal axis, the projection protrudes more than other portions of the opposite surface in the thickness direction, and a maximum thickness of the distal portion is smaller than a maximum width of the distal portion in a width direction perpendicular to the thickness direction.

8 Claims, 8 Drawing Sheets

(51) Int. Cl.
  *A61B 18/00* (2006.01)
  *A61B 17/28* (2006.01)
  *A61N 7/00* (2006.01)

(52) U.S. Cl.
  CPC ......... *A61B 2017/2825* (2013.01); *A61B 2017/320078* (2017.08); *A61B 2017/320094* (2017.08); *A61B 2017/320095* (2017.08); *A61B 2018/0063* (2013.01); *A61B 2018/00083* (2013.01); *A61B 2018/00101* (2013.01); *A61B 2018/00529* (2013.01); *A61B 2018/00607* (2013.01); *A61B 2018/00994* (2013.01); *A61N 7/00* (2013.01)

(58) Field of Classification Search
  CPC ....... A61B 2017/320074; A61B 2017/320075; A61B 2017/320077; A61B 2017/320069; A61B 2017/320082; A61B 2017/320095; A61B 2017/320098; A61B 17/3201; A61B 17/3209; A61B 17/3211; A61B 2017/32007; A61B 2017/320071; A61B 2017/320078; A61B 2017/320084; A61B 2017/320088; A61B 2017/320089; A61B 2017/32009; A61B 2017/320093; A61B 2017/320094; A61B 2017/320097
  See application file for complete search history.

(56) References Cited

U.S. PATENT DOCUMENTS

| | | | |
|---|---|---|---|
| 6,423,082 B1 * | 7/2002 | Houser | A61B 17/32006 606/169 |
| 2008/0132927 A1 | 6/2008 | Sakai | |
| 2008/0234710 A1 | 9/2008 | Neurohr et al. | |
| 2011/0288451 A1 | 11/2011 | Sanai et al. | |
| 2014/0142573 A1 * | 5/2014 | Masuda | A61B 18/1445 606/51 |
| 2014/0163595 A1 | 6/2014 | Witt et al. | |
| 2014/0277029 A1 | 9/2014 | Messerly et al. | |
| 2015/0148831 A1 * | 5/2015 | Faller | A61B 17/32009 606/169 |

FOREIGN PATENT DOCUMENTS

| | | |
|---|---|---|
| EP | 2 105 100 A1 | 9/2009 |
| JP | H08-505801 A | 6/1996 |
| JP | 2001-309925 A | 11/2001 |
| JP | 2008-136845 A | 6/2008 |
| WO | WO 2014/088899 A1 | 6/2014 |
| WO | WO 2015/029518 A1 | 3/2015 |

OTHER PUBLICATIONS

Japanese Office Action dated Feb. 7, 2017 in related Japanese Patent Application No. 2016-570065.
English translation of International Search Report dated Jul. 5, 2016 in related International Application No. PCT/JP2016/064640.
Extended Supplementary European Search Report dated Jan. 21, 2019 in European Patent Application No. 16 79 9879.8.
Chinese Office Action dated Jul. 12, 2019 in Chinese Patent Application No. 201680014388.8.
Chinese Office Action dated Mar. 3, 2020 in Chinese Patent Application No. 201680014388.8.

* cited by examiner

SURGICAL APPARATUS

CROSS-REFERENCE TO RELATED APPLICATION

The present application is a continuation of PCT/JP2016/064640 filed on May 17, 2016, which is based upon and claims the benefit to JP 2015-107773 filed on May 27, 2015, the entire contents of each of which are incorporated herein by reference.

BACKGROUND

Field

The present application relates to a vibration transmitting member and a surgical apparatus.

Prior Art

For example, US 2011/288451 A1 discloses a surgical apparatus enabling dissection of living tissue during coagulation of the living tissue with use of high-frequency output and ultrasonic output in a state in which the living tissue is grasped.

A distal end of a vibration transmitting member of such a surgical apparatus and a clamp member opposed to the vibration transmitting member to enable approach to and separation from the vibration transmitting member by turning are formed to be thin in consideration of a dissection performance of living tissue. Thus, a contact area between the vibration transmitting member and clamp member and the living tissue is small. Accordingly, such a surgical apparatus may not be suitable when treatment of the removal of living tissue such as a liver is conducted. Also, when the treatment of the removal of the living tissue is conducted, a blood vessel may be buried. In this case, surface pressure between the vibration transmitting member and clamp member and the blood vessel at the time of grasping the blood vessel is required to be lowered.

SUMMARY

An object is to provide a vibration transmitting member and a surgical apparatus enabling treatment of the removal of living tissue such as a liver to be conducted appropriately and enabling a blood vessel or the like buried in the living tissue to be grasped appropriately.

Accordingly, a vibration transmitting member is provided for use with a clamp member. The vibration transmitting member being provided with vibration from an ultrasonic transducer, the vibration transmitting member comprising: a body having a distal portion with a surface and an opposite surface, the body further having a proximal portion; wherein: the body extending along a longitudinal axis extending from the proximal portion toward the distal portion, the surface configured to oppose the clamp member, the surface having a ridge extending along the longitudinal axis, the ridge configured to extend toward the clamp member in a thickness direction of the distal portion more than other portions of the surface, the opposite surface configured to oppose the surface, the opposite surface having a projection extending along the longitudinal axis, the projection configured to protrude more than other portions of the opposite surface in the thickness direction, and a maximum thickness of the distal portion through the ridge and the projection in the thickness direction is smaller than a maximum width of the distal portion in a width direction perpendicular to the thickness direction.

DESCRIPTION OF PREFERRED EMBODIMENTS

Hereinbelow, embodiments will be described with reference to the drawings.

A first embodiment will be described with reference to FIGS. 1 to 3D.

Figure 1:
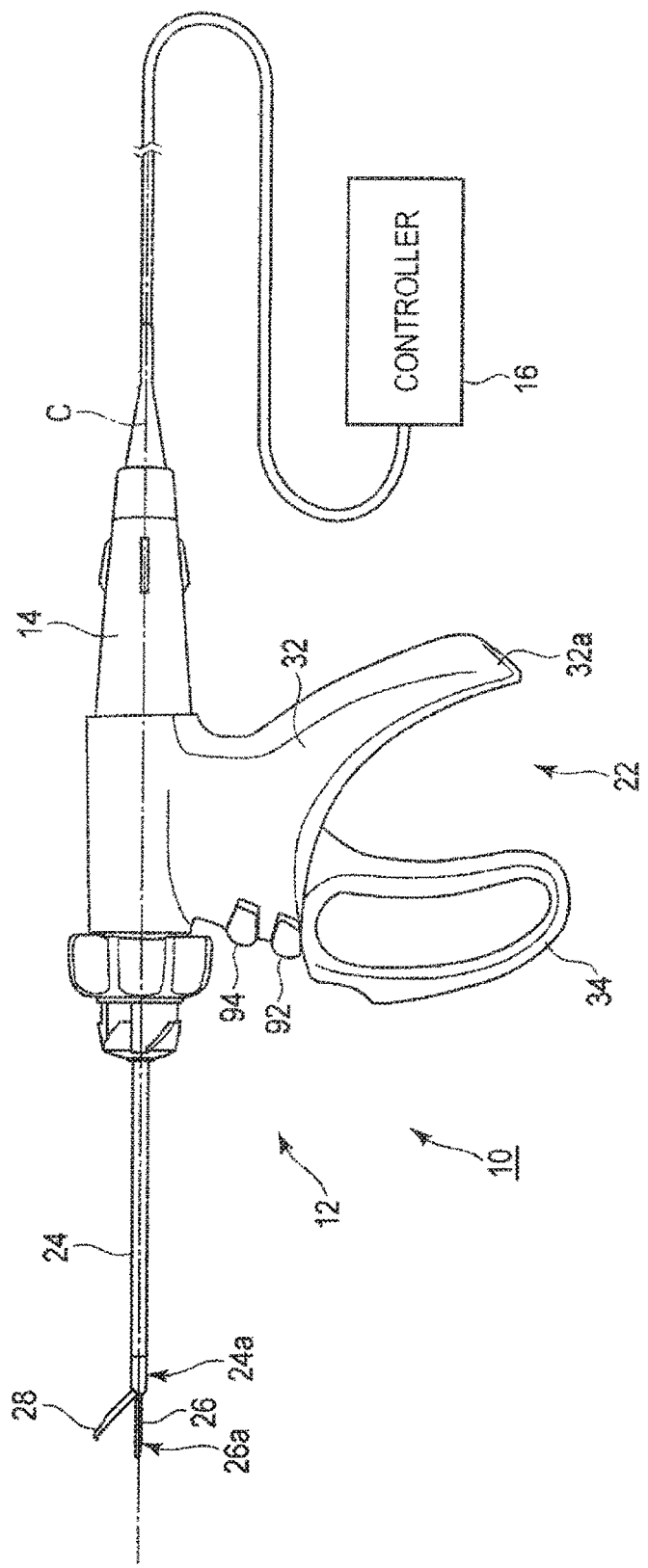
FIG. 1 illustrates a schematic view of a surgical system according to first to fifth embodiments.

As illustrated in FIG. 1, a surgical system 10 according to the present embodiment includes a surgical apparatus 12, an ultrasonic transducer 14, and a controller 16. The controller 16 includes an energy source (not illustrated) supplying the ultrasonic transducer 14 with energy generating appropriate ultrasonic vibration. The ultrasonic transducer 14 is arranged at a proximal end of a below-mentioned vibration transmitting member 26 and generates ultrasonic vibration to enable the vibration to be transmitted from the proximal portion to a distal portion along a longitudinal axis (center axis) C of the vibration transmitting member 26.

The not-illustrated energy source of the controller 16 can generate the ultrasonic vibration in the transducer 14 and apply high-frequency output to living tissue grasped between the below-mentioned vibration transmitting member 26 serving as a first electrode of the surgical apparatus 12 and electrode portions 56a and 56b included in a below-mentioned clamp member 28 serving as a second electrode. The controller can 16 include a processor including a CPU, an ASIC, or the like.

As illustrated in FIGS. 1 to 3A, the surgical apparatus 12 includes a handle unit 22, a cylindrical sheath 24, the vibration transmitting member (rod-like member) 26, and the clamp member 28 used with the vibration transmitting member 26 and enabling approach to and separation from the vibration transmitting member 26. The vibration transmitting member 26 is used with the clamp member 28 and can transmit vibration from the ultrasonic transducer 14.

Figure 2:
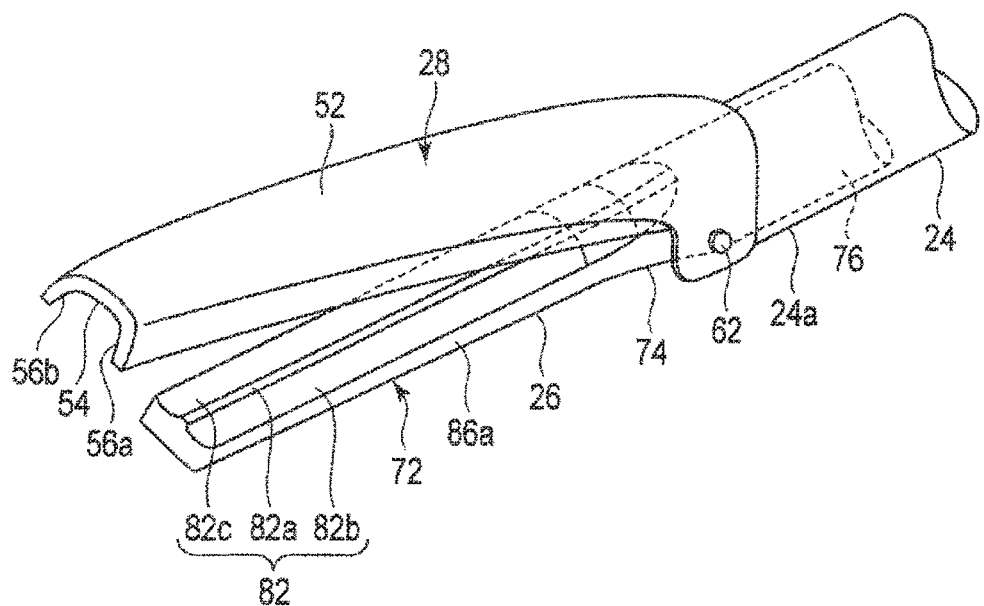
FIG. 2 illustrates a schematic perspective view of a part around a distal portion of a vibration transmitting member and a clamp member in a surgical apparatus of the surgical system according to the first embodiment.
Figure 3A:
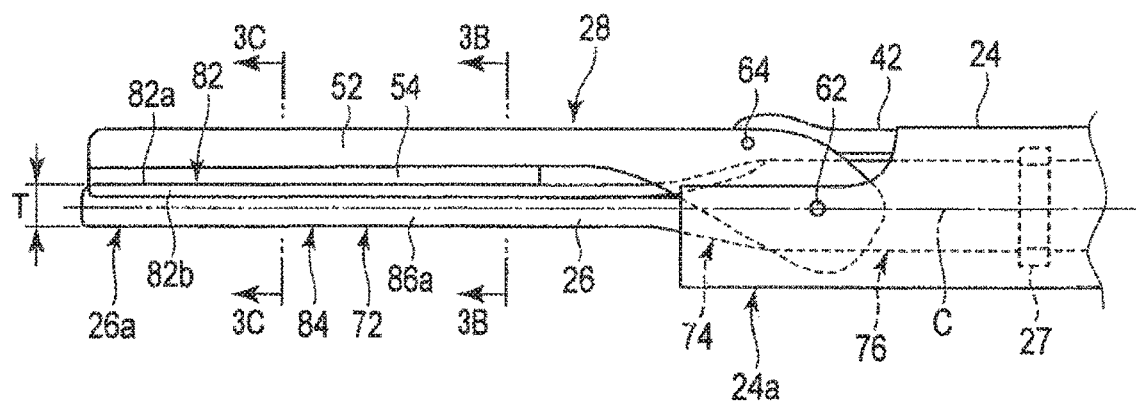
FIG. 3A illustrates a schematic side view of the part around the distal portion of the vibration transmitting member and the clamp member in the surgical apparatus of the surgical system according to the first embodiment.

As illustrated in FIG. 1, the handle unit 22 includes a housing 32 including a fixed handle 32a, and a movable handle 34. Inside the sheath 24, a driving member 42 (refer to FIG. 3A) operating along an axial direction of the center axis C, interlocking with an operation of the movable handle 34, is arranged. The driving member 42 can be formed in a cylindrical shape concentrically with the sheath 24. The movable handle 34 can move between a separation position (open position) illustrated in FIG. 1 separating from the fixed handle 32a of the housing 32 and an approach position (close position) approaching to the fixed handle 32a of the housing 32. In the present embodiment, when the movable handle 34 is at the separation position, the clamp member 28 is at a separation position from a distal portion (treatment portion) 26a of the vibration transmitting member 26 as illustrated in FIGS. 1 and 2. Also, when the movable handle 34 is at the approach position, the clamp member 28 is at an approach position to the distal portion 26a of the vibration transmitting member 26 as illustrated in FIG. 3A.

Meanwhile, it is to be understood that the clamp member 28 may be at the approach position to the distal portion 26a of the vibration transmitting member 26 when the movable handle 34 is at the separation position and that the clamp member 28 may be at the separation position from the distal portion 26a of the vibration transmitting member 26 when the movable handle 34 is at the approach position.

Figure 3B:
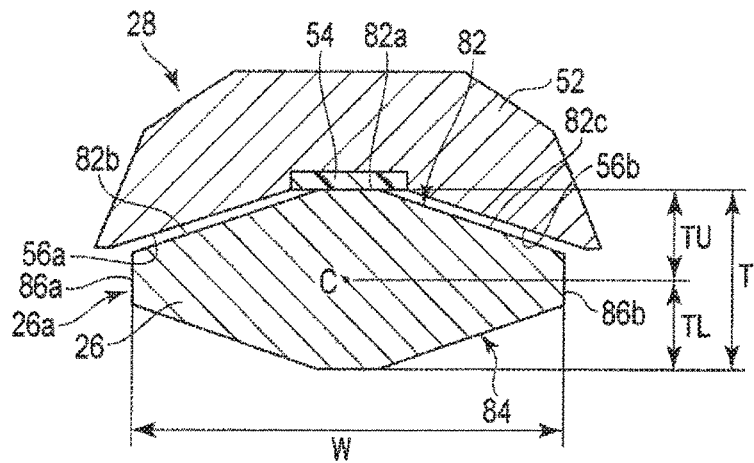
FIG. 3B illustrates a schematic horizontal cross-sectional view along line 3B-3B in FIG. 3A of the part around the distal portion of the vibration transmitting member and the clamp member in the surgical apparatus of the surgical system according to the first embodiment.
Figure 3C:
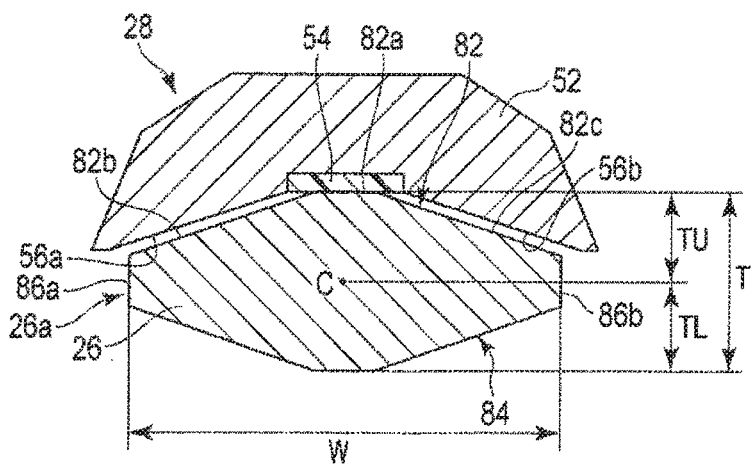
FIG. 3C illustrates a schematic horizontal cross-sectional view along line 3C-3C in FIG. 3A of the part around the distal portion of the vibration transmitting member and the clamp member in the surgical apparatus of the surgical system according to the first embodiment.
Figure 3D:
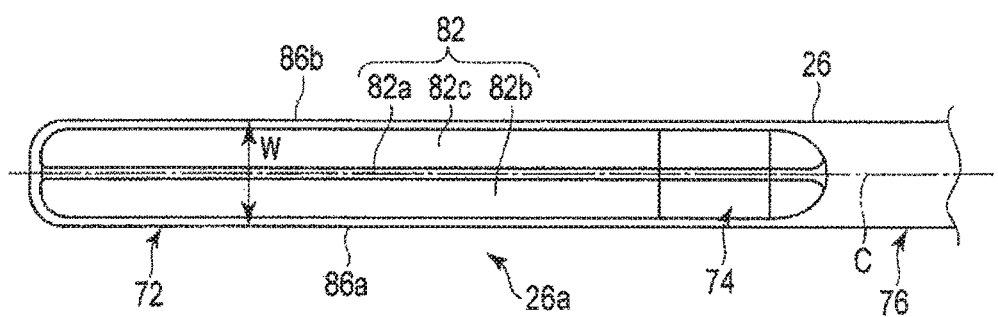
FIG. 3D illustrates a schematic top view of the distal portion of the vibration transmitting member in the surgical apparatus of the surgical system according to the first embodiment.

At a distal portion 24a of the sheath 24, the clamp member 28 is turnably supported. As illustrated in FIGS. 2, 3B, and 3C, the clamp member 28 includes a clamp member main body (turning body) 52, a pressing pad 54 provided in the main body 52, and the pair of electrode portions 56a and 56b provided in the main body 52.

The main body 52 of the clamp member 28 may be formed by a single body or by plural bodies such as two bodies. In a case in which the main body 52 is formed by the plural bodies, a known so-called seesaw jaw or wiper jaw can be used.

The main body 52 of the clamp member 28 is supported at the distal portion 24a of the sheath 24 to be turnable by a main turning shaft 62, for example. The main body 52 is supported at a distal portion of the driving member 42 to be turnable by a moving and turning shaft (distal-side turning shaft) 64. The main turning shaft 62 and the moving and turning shaft (distal-side turning shaft) 64 can be parallel to each other and can be perpendicular to the center axis C. When the driving member 42 moves forward along the center axis (longitudinal axis) C with respect to the sheath 24 in response to an operation of the movable handle 34 with respect to the housing 32, the driving member 42 presses the main body 52 to a front side of the sheath 24 approximately in parallel with the center axis C by means of the moving and turning shaft 64. Since positional relationship among the main turning shaft 62, the main body 52, and the distal portion 24a of the sheath 24 does not change, the main body 52 closes toward the distal portion 26a of the vibration transmitting member 26. Conversely, when the driving member 42 moves backward along the center axis C with respect to the sheath 24 in response to an operation of the movable handle 34, the driving member 42 pulls the main body 52 to a backside of the sheath 24 in parallel with the center axis C by means of the moving and turning shaft 64. Thus, the main body 52 opens away from the distal portion 26a of the vibration transmitting member 26. That is, the main body 52 of the clamp member 28 is movable between the approach position (close position) approaching to the vibration transmitting member 26 and the separation position (open position) separating from the vibration transmitting member 26 by means of the operations of the movable handle 34.

The pressing pad 54 is provided at a position in the main body close to a below-mentioned treatment surface 82 at the distal portion 26a of the vibration transmitting member 26 in a state of being opposed to the treatment surface 82. The pressing pad 54 is arranged between the electrode portions 56a and 56b in the main body 52. The pressing pad 54 abuts on a below-mentioned dissecting area 82a of the treatment surface 82 at the distal portion 26a of the vibration transmitting member 26 when the main body 52 is at the approach position and separates from the treatment surface 82 at the distal portion 26a of the vibration transmitting member 26 along with movement of the main body 52 when the main body 52 is at the separation position. The pressing pad 54 is made of a material having electric insulation, heat resistance, and abrasion resistance. As a material for the pressing pad 54, a PTFE material can be used, for example.

In the present embodiment, in a case in which the clamp member 28 is at the approach position, especially the dissecting area 82a of the treatment surface 82 at the distal portion 26a of the vibration transmitting member 26 can abut on the pressing pad 54 but does not abut on the electrode portions 56a and 56b. Thus, when the treatment surface 82 at the distal portion 26a of the vibration transmitting member 26 is used as one electrode while the electrode portions 56a and 56b of the clamp member 28 are used as the other electrode, and living tissue is clamped between the electrodes, bipolar treatment can be conducted to the living tissue.

Meanwhile, a heater may be used instead of the electrode portions 56a and 56b, or an equal material to the pressing pad 54 may be provided on the surface instead of the electrode portions 56a and 56b.

The vibration transmitting member (rod-like member) 26 is inserted into the sheath 24. The vibration transmitting member 26 is made of a material having a good vibration transmitting characteristic such as a titanium alloy material and an aluminum alloy material. The vibration transmitting member 26 extends from the proximal portion to which the ultrasonic transducer 14 is connected toward the distal portion. In the vibration transmitting member 26, vibration is transmitted from the proximal portion toward the distal portion in response to input of vibration from the ultrasonic transducer 14. The vibration transmitting member 26 is conductive when the vibration transmitting member 26 is used as one of high-frequency electrodes. The vibration transmitting member 26 can be arranged on the center axis C of the sheath 24.

From the proximal end to the distal end of the vibration transmitting member 26, vibration having an appropriate frequency is transmitted by the ultrasonic transducer 14 attached to the proximal end of the vibration transmitting member 26. Thus, a length from the proximal portion to the distal portion of the vibration transmitting member 26 is set in accordance with the frequency of the vibration output by the ultrasonic transducer 14. Particularly, the distal end of the vibration transmitting member 26 is set at an antinode position of the vibration since the distal end conducts appropriate treatment to living tissue in a state in which the vibration is transmitted. An outer circumferential surface of the vibration transmitting member 26 located at a node position of the vibration in a state in which the vibration is transmitted to the vibration transmitting member 26 is provided between the outer circumferential surface and an inner circumferential surface of the sheath 24 with a ring-like member 27 having electric insulation and heat resistance. That is, in the treatment portion 26a of the vibration transmitting member 26, a distal end corresponds to the antinode position of the vibration while a proximal end corresponds to the node position of the vibration inside the sheath 24, and a length of the treatment portion 26a corresponds to a quarter wavelength of the vibration (vibrational wave) output by the ultrasonic transducer 14. Meanwhile, the treatment portion 26a can be formed to be symmetric or approximately symmetric across an opening/closing surface including the center axis C to which the clamp member 28 turns. Also, the treatment portion 26a can be formed to be symmetric or approximately symmetric across the center axis C in a direction along an opening/closing direction of the clamp member 28.

As illustrated in FIG. 3A, the distal portion of the treatment portion 26a of the vibration transmitting member 26 according to the present embodiment includes a treatment area (parallel area) 72 provided to be parallel to or approximately parallel to the center axis C and adapted to conduct treatment to living tissue, a middle area 74 formed on a proximal side of the treatment area 72, and a rod-like area 76 formed on a proximal side of the middle area 74. The rod-like area 76 can have an approximately equal diameter, for example, has a circular horizontal cross-sectional surface, and is formed in a rod shape at an appropriate position along the center axis C. Meanwhile, in the present embodiment, a first node position of the vibration from the distal end is located in the rod-like area 76. In the middle area 74, a horizontal cross-sectional surface thereof smoothly changes from the rod-like area 76 at the proximal end thereof to the treatment area 72 at a distal end thereof. In the present embodiment, in the middle area 74, a thickness along the opening/closing direction in which the clamp member 28 moves by turning can be smaller gradually from the proximal end to the distal end along the center axis C in FIGS. 3A and 3D. At this time, the middle area 74 can be formed to have a symmetric or approximately symmetric thickness across the center axis C. Conversely, in the present embodiment, in the middle area 74, a length in a width direction perpendicular to the opening/closing direction of the clamp member 28 can be approximately equal regardless of an appropriate position along the center axis C in FIGS. 3A and 3D.

The treatment area 72 includes the treatment surface 82, a back surface 84 opposed to the treatment surface 82, and side surfaces 86a and 86b between the treatment surface 82 and the back surface 84. In the treatment area 72 of the treatment portion 26a, a thickness T along the opening/closing direction in which the clamp member 28 is to move by turning is smaller than a width W along the width direction perpendicular to the opening/closing direction. Thus, the treatment portion 26a is formed approximately in a flat shape. In the present embodiment, the width W in the width direction can be equal from a distal portion of the treatment area 72 of the treatment portion 26a to an appropriate position such as the rod-like area 76 at the proximal portion of the treatment portion 26a. As illustrated in FIGS. 3B and 3C, in the present embodiment, a thickness (height) TU of an upper part and a thickness (height) TL of a lower part with respect to the longitudinal axis C can be equal.

The treatment surface 82 includes the dissecting area 82a enabling abutment on the pressing pad 54 and transmitting ultrasonic vibration thereto to enable dissection of living tissue and sealing areas 82b and 82c formed adjacent to the dissecting area 82a in the width direction and enabling coagulation and sealing of the living tissue by means of high-frequency output generated by electric conduction between the sealing areas 82b and 82c and the electrode portions 56a and 56b of the clamp member 28 via the living tissue. As illustrated in FIGS. 3B and 3C, the dissecting area 82a and the sealing areas 82b and 82c are formed along the longitudinal axis C. The dissecting area 82a is at a top portion along the opening/closing direction of the clamp member 28 and has an appropriate width, for example, to form a ridge (ridge line). This dissecting area (ridge) 82a extends along the longitudinal axis C and is located on the opening/closing surface to which the clamp member 28 is to move by turning. The sealing areas 82b and 82c are formed successively to the dissecting area 82a and are respectively formed as inclined surfaces elongated along the longitudinal axis C. The ridge 82a is configured to extend toward the clamp member 28 in a thickness direction (the opening/closing direction) of the distal portion 26a more than other portion of the treatment surface 82. A thickness of the distal portion 26a through the ridge 82a in the thickness direction is smaller than a width of the distal portion 26a in a width direction perpendicular to the thickness direction.

The sealing areas 82b and 82c may be flat surfaces or curved surfaces. As illustrated in FIGS. 3B and 3C, the thickness T of the treatment area 72 is thinner at a position farther than a position including the center axis C (position including the dissecting area 82a) along the width direction.

As illustrated in FIG. 1, the housing 32 is provided with first and second switches 92 and 94. When the first switch 92 is pressed, bipolar high-frequency output is performed between the vibration transmitting member 26 serving as the first electrode and the electrode portions 56a and 56b of the clamp member 28 serving as the second electrode. Thus, by pressing the first switch 92, coagulation of living tissue or sealing of a blood vessel is conducted between the vibration transmitting member 26 and the electrode portions 56a and 56b of the clamp member 28. When the second switch 94 is pressed, ultrasonic output and bipolar high-frequency output are performed. Thus, living tissue is dissected while the living tissue is coagulated, or a blood vessel is dissected while the blood vessel is sealed.

Next, actions of the surgical system 10 according to the present embodiment will be described. Here, description is provided, using liver tissue as a treated target, for example.

The movable handle 34 is moved closer to the fixed handle 32a of the housing 32 to move the clamp member 28 closer to the treatment surface 82 of the vibration transmitting member 26. Liver tissue is then grasped between the pressing pad 54 and the electrode portions 56a and 56b of the clamp member 28 and the treatment surface 82 of the vibration transmitting member 26. At this time, the width W of the treatment surface 82 of the vibration transmitting member 26 is formed to be longer than the thickness T, and a width of the clamp member 28 is similarly formed to be long to correspond to the width W of the treatment surface 82 of the vibration transmitting member 26. Thus, an area of the treatment surface is formed to be large. Accordingly, since the width of the treatment surface 82 is long, a contact area of the treatment surface 82 of the vibration transmitting member 26 and the clamp member 28 is large at the time of contacting the liver tissue, and the treatment surface 82 of the vibration transmitting member 26 and the clamp member 28 are easily grasp the liver tissue. The pressing pad 54 and the electrode portions 56a and 56b of the clamp member 28 and the treatment surface 82 of the vibration transmitting member 26 are formed to clamp the liver tissue therebetween. Also, when the living tissue is grasped between the pressing pad 54 and the electrode portions 56a and 56b of the clamp member 28 and the treatment surface 82 of the vibration transmitting member 26, and a compressing force (grasping force) is applied, the compressing force is distributed over the contact surface since the contact area between the treatment surface 82 and the living tissue is large. Accordingly, in the treatment surface 82, an action of widely pressing and compressing the living tissue is larger than an action of dissecting the living tissue by focusing the compressing force on a part. The treatment surface 82 is suitable for the removal of the liver tissue, especially liver parenchyma.

Meanwhile, at this time, no operation of the first switch 92 or the second switch 94 is required. That is, in a case in which treatment of the removal of the liver tissue is conducted by means of the surgical apparatus 12 according to the present embodiment, the high-frequency output and the ultrasonic output are not required.

In case of grasping a blood vessel between the clamp member 28 and the treatment surface 82 of the vibration transmitting member 26, the contact area between the treatment surface 82 of the vibration transmitting member 26 and the living tissue is large. Thus, surface pressure when the blood vessel is grasped between the clamp member 28 and the treatment surface 82 of the vibration transmitting member 26 is distributed. Accordingly, when the blood vessel in the liver tissue is grasped between the clamp member 28 and the treatment surface 82 of the vibration transmitting member 26, it is possible to prevent the blood vessel from being damaged and bleeding by a mechanical force of the compressing force (grasping force).

The movable handle 34 is moved away from the fixed handle 32a of the housing 32 to move the clamp member 28 away from the treatment surface 82 of the vibration transmitting member 26. The movable handle 34 is then moved closer to the fixed handle 32a of the housing 32 again to move the clamp member 28 closer to the treatment surface 82 of the vibration transmitting member 26, and adjacent liver tissue is removed in a similar manner to the above.

As described above, when the liver tissue is removed, the blood vessel in the liver may appear. In this case, the blood vessel is grasped between the pressing pad 54 of the clamp member 28 and the treatment surface 82 of the vibration transmitting member 26. When the first switch 92 is pressed in this state, the blood vessel is coagulated by the action of the high-frequency output. Also, when the second switch 94 is pressed, the blood vessel is dissected mainly by the action of the ultrasonic vibration while the blood vessel is coagulated mainly by the action of the high-frequency output. Specifically, the blood vessel is dissected at the dissecting area 82a of the treatment surface 82 by the action of the ultrasonic output while the blood vessel is coagulated at the sealing areas 82b and 82c of the treatment surface 82 by the action of the high-frequency output.

As described above, the present embodiment can achieve the following advantages.

The width W of the treatment surface 82 in the vibration transmitting member 26 opposed to the clamp member 28 is wider than the thickness T, and the vibration transmitting member 26 is formed approximately in the flat shape. Accordingly, an area in the treatment surface 82 of the vibration transmitting member 26 abutting on liver tissue or the like can be large, and tissue having a larger area can be clamped and compressed between the clamp member 28 and the treatment surface 82. Also, even in a case in which a blood vessel is unintentionally grasped when the treatment surface 82 grabs the liver tissue or the like, the contact area between the blood vessel and the treatment surface 82 is set to be large, and the surface pressure of the treatment surface 82 to the blood vessel can be distributed. Accordingly, when the blood vessel is grasped between the treatment surface 82 of the vibration transmitting member 26 and the clamp member 28, it is possible to prevent the blood vessel from being damaged and bleeding by a mechanical force of the compressing force (grasping force).

When the blood vessel is grasped, the blood vessel can be coagulated by the high-frequency output. Also, the blood vessel can be dissected while being coagulated by the high-frequency output and the ultrasonic output.

Thus, the present embodiment can provide the vibration transmitting member 26 and the surgical apparatus 12 enabling treatment of the removal of living tissue such as a liver to be conducted appropriately and enabling a blood vessel or the like buried in the living tissue to be grasped appropriately.

Next, a second embodiment will be described with reference to FIGS. 4A to 4D. The present embodiment is a modification example of the first embodiment. Members similar to or having similar functions to those described in the first embodiment are shown with the same reference numerals as much as possible, and detailed description of such similar components is omitted.

As illustrated in FIGS. 4A to 4D, the treatment portion 26a as the distal portion of the vibration transmitting member 26 according to the present embodiment has a different width in the width direction and a different horizontal cross-sectional shape depending on a position along the longitudinal axis C.

The treatment area 72 of the treatment portion 26a can be formed to be symmetric or approximately symmetric across the center axis C in the width direction. The treatment area 72 of the treatment portion 26a includes a distal area 72a, a width change area 72b provided on a proximal side of the distal area 72a, and a proximal area 72c provided on a proximal side of the width change area 72b. That is, the treatment area 72 of the treatment portion 26a includes the width change area 72b between the distal area 72a and the proximal area 72c, as well as the distal area 72a and the proximal area 72c, in a quarter wavelength area of the vibrational wave output by the ultrasonic transducer 14 from the distal portion to the proximal side (area approximately over the entire length of the treatment portion 26a). The distal area 72a illustrated in FIG. 4B has an approximately constant width W1 in the width direction and an approximately constant horizontal cross-sectional shape from a position close to a distal end thereof to the proximal end. As a matter of course, the distal end of the distal area 72a is formed in an obtuse shape. As illustrated in FIG. 4D, a width of the width change area 72b in the width direction is gradually, such as successively, reduced from the proximal end of the distal area 72a to a distal end of the proximal area 72c. That is, the width change area 72b has a wider width in the width direction and a larger horizontal cross-sectional area at a position closer to the distal area 72a and has a shorter width in the width direction and a smaller horizontal cross-sectional area at a position closer to the proximal area 72c. Further, the proximal area 72c has an approximately constant width W2 in the width direction and an approximately constant horizontal cross-sectional shape from a position close to the distal end thereof to a proximal end thereof. Accordingly, the width W1 of the distal area 72a in the width direction perpendicular to the longitudinal axis C is wider than the width W2 of the proximal area 72c in the width direction. That is, in the treatment portion 26a, the width W1 in the width direction on a cross-section of the distal area 72a perpendicular to the longitudinal axis C is wider than the width W2 in the width direction on a cross-section of the proximal area 72c.

Figure 4A:
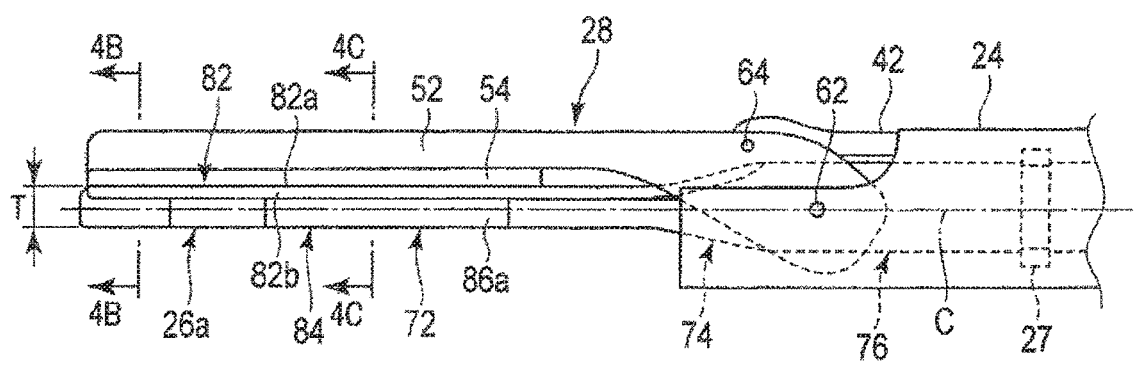
FIG. 4A illustrates a schematic side view of the part around the distal portion of the vibration transmitting member and the clamp member in the surgical apparatus of the surgical system according to the second embodiment.
Figure 4B:
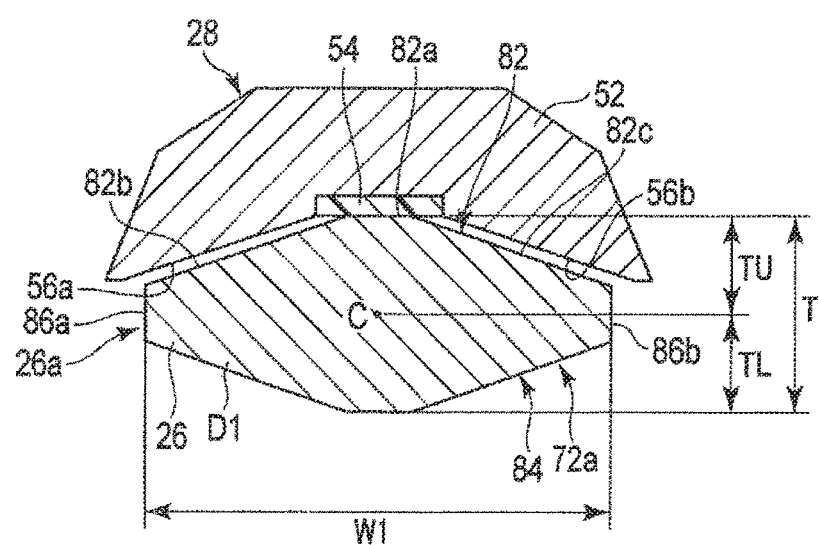
FIG. 4B illustrates a schematic horizontal cross-sectional view along line 4B-4B in FIG. 4A of the part around the distal portion of the vibration transmitting member and the clamp member in the surgical apparatus of the surgical system according to the second embodiment.
Figure 4C:
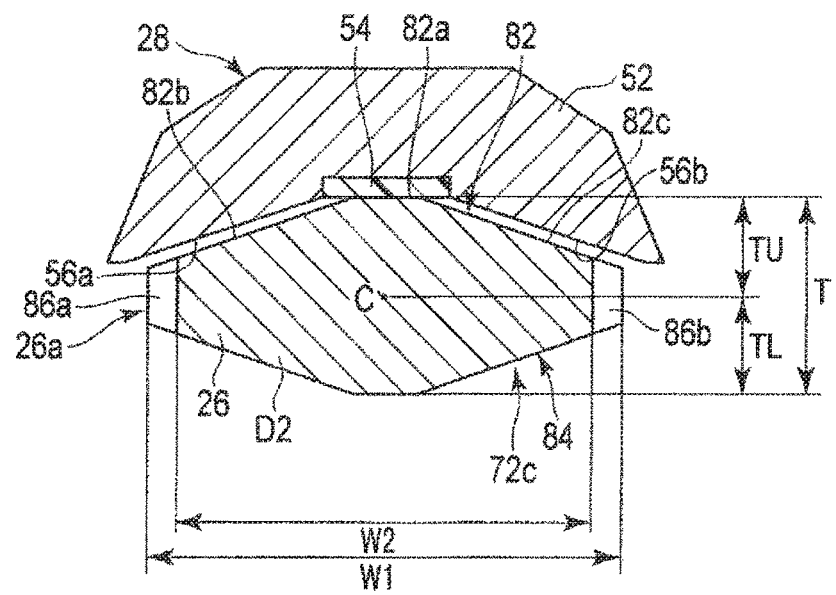
FIG. 4C illustrates a schematic horizontal cross-sectional view along line 4C-4C in FIG. 4A of the part around the distal portion of the vibration transmitting member and the clamp member in the surgical apparatus of the surgical system according to the second embodiment.
Figure 4D:
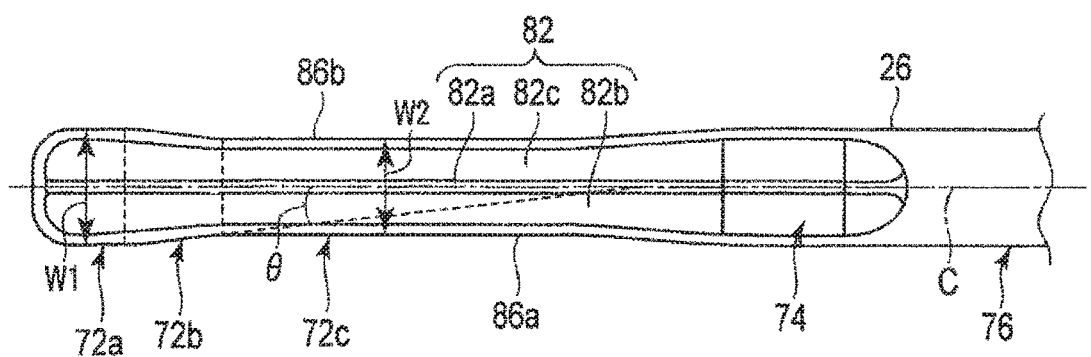
FIG. 4D illustrates a schematic top view of the distal portion of the vibration transmitting member in the surgical apparatus of the surgical system according to the second embodiment.

Also, a cross-sectional area D1 in the distal area 72a illustrated in FIG. 4B is larger than a cross-sectional area D2 in the proximal area 72c illustrated in FIG. 4C. Also, a cross-sectional area of the width change area 72b is as large as a cross-sectional area between the cross-sectional area D1 in the distal area 72a and the cross-sectional area D2 in the proximal area 72c although it is not illustrated. More specifically, the cross-sectional area of the width change area 72b is gradually reduced from the proximal end of the distal area 72a to the distal end of the proximal area 72c. The cross-sectional area of the width change area 72b can correspond at a distal end thereof to the cross-sectional area D1 of the proximal end of the distal area 72a and correspond at the proximal end thereof to the cross-sectional area D2 of the distal end of the proximal area 72c. Accordingly, the cross-sectional area D1 of the distal area 72a perpendicular to the longitudinal axis C is larger than the cross-sectional area D2 of the proximal area 72c perpendicular to the longitudinal axis C.

In the treatment area 72 of the treatment portion 26a, the width change area 72b and the distal area 72a are formed to be wider than the proximal area 72c. That is, the proximal area 72c is formed to be narrower than the width change area 72b and the distal area 72a. Thus, in a case in which the width change area 72b or the distal area 72a is checked from the proximal side of the vibration transmitting member 26 and the clamp member 28 with use of an endoscope (not illustrated), for example, the width change area 72b or the distal area 72a can be checked through a part at which no flesh exists. Accordingly, the treatment portion 26a of the vibration transmitting member 26 according to the present embodiment is formed to facilitate checking of a treatment state with use of the endoscope.

As illustrated in FIG. 4D, when a line along an external edge (side surface 86a or 86b) in the width direction of the width change area 72b is virtually extended toward the longitudinal axis C, an angle θ between the longitudinal axis C and the virtual line illustrated by the dashed line can be set to 30° or less, for example. It is empirically found that, when the angle θ is around 5°, for example, generation of mist, that is, generation of cavitation, can be restricted in the width change area 72b between the distal area 72a and the proximal area 72c in a state in which vibration is transmitted from the ultrasonic transducer 14 to the vibration transmitting member 26. This angle θ can be changed to 10°, 20°, or the like as appropriate. Also, although each of the side surfaces 86a and 86b of the width change area 72b is a linearly-extended inclined surface in the above embodiment, each of the side surfaces 86a and 86b may be formed to change the width continuously by combining a plurality of inclined surfaces. For example, each of the side surfaces 86a and 86b may be formed to change the width from the proximal area 72c toward the distal area 72a in a multistage manner, in which an area whose angle θ between the longitudinal axis C and the virtual line is 5°, an area whose angle θ is 10°, and the like are arranged. Also, although each of the side surfaces 86a and 86b of the width change area 72b is the linearly-extended inclined surface in the above embodiment, each of the side surfaces 86a and 86b of the width change area 72b may be formed as a curved surface, and the angle θ between a tangential line of the curved surface and the longitudinal axis C may be 30° or less.

Especially at the time of treatment, the distal end of the treatment portion 26a of the vibration transmitting member 26 and the distal end of the clamp member 28 are moved finely. The width change area 72b and the proximal area 72c are formed to be narrower than the distal area 72a. Thus, even in a case in which the temperature of the treatment portion 26a of the vibration transmitting member 26 is higher than a temperature denaturalizing protein of living tissue (e.g., approximately 60° C.) due to the high-frequency output or the like, for example, the width change area 72b and the proximal area 72c are harder to contact the living tissue than in a state in which the width change area 72b and the proximal area 72c have the same widths as that of the distal area 72a. Accordingly, by using the vibration transmitting member 26 according to the present embodiment, generation of thermal spread can be restricted when the treatment portion 26a of the vibration transmitting member 26 and the clamp member 28 are moved as appropriate.

Thus, the present embodiment can provide the vibration transmitting member 26 and the surgical apparatus 12 enabling restriction of thermal spread while securing insertability into a small hole and visibility of a distal portion.

Next, a third embodiment will be described with reference to FIG. 5. The present embodiment is a modification example of the first and second embodiments. Members similar to or having similar functions to those described in the first and second embodiments are shown with the same reference numerals as much as possible, and detailed description of such similar components is omitted. It is to be understood in the present embodiment that the treatment portion 26a of the vibration transmitting member 26 may be either one having a constant width as described in the first embodiment or one having the distal area 72a, the width change area 72b, and the proximal area 72c and changing a width depending on a position as described in the second embodiment.

Figure 5:
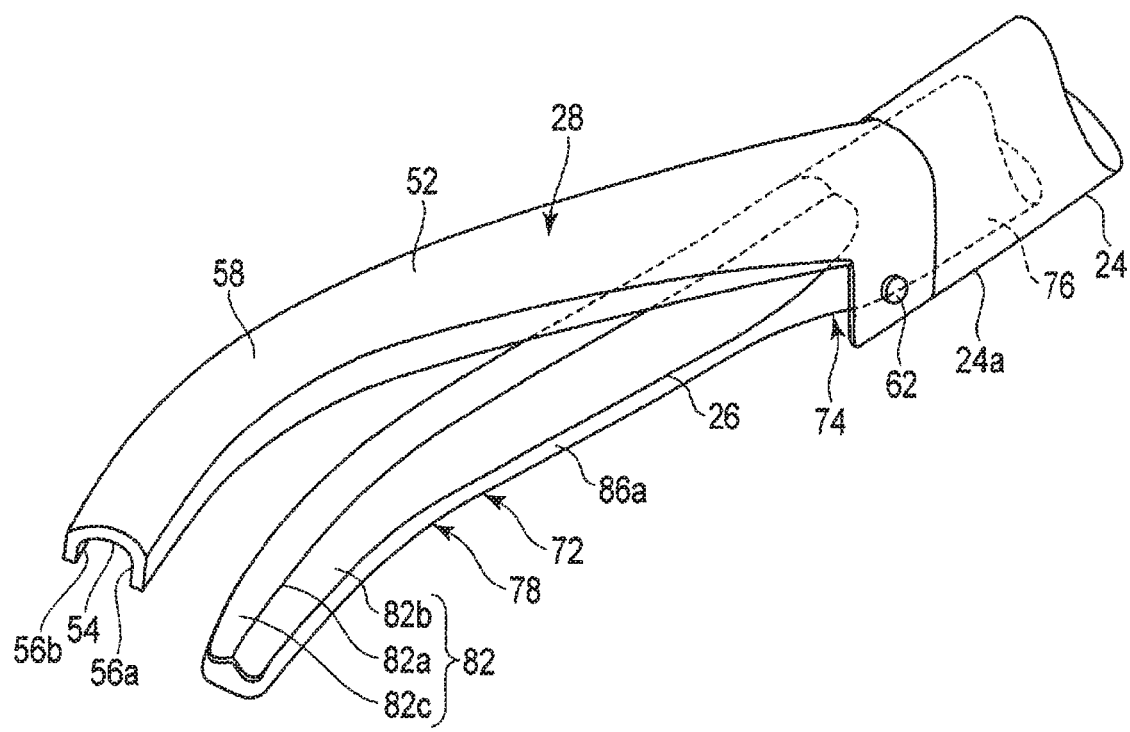
FIG. 5 illustrates a schematic perspective view of the part around the distal portion of the vibration transmitting member and the clamp member in the surgical apparatus of the surgical system according to the third embodiment.

As illustrated in FIG. 5, the treatment area 72 of the distal portion 26a of the vibration transmitting member 26 is bent at a bent portion 78 in one direction from a straight state. Similarly, the clamp member 28, as well as the treatment portion 26a of the vibration transmitting member 26, is bent at a bent portion 58 in one direction from a straight state. Here, as an example, a part from the distal end to the bent portion 78 of the vibration transmitting member 26 is bent, and a part from the bent portion 78 to the proximal side is straight. Similarly, a part from the distal end to the bent portion 58 of the clamp member 28 is bent, and a part from the bent portion 58 to the proximal side is straight.

Meanwhile, it is to be understood that a part from the distal end of the treatment area 72 to the distal end of the middle area 74 in the treatment portion 26a of the vibration transmitting member 26 can be bent to form the bent portion 78. That is, the treatment portion 26a of the vibration transmitting member 26 has only to include the bent portion 78 between the distal end of the treatment area 72 and the distal end of the middle area 74. Thus, the treatment area 72 of the treatment portion 26a includes the bent portion 78 between the distal end of the treatment area 72 and the proximal end of the treatment area 72 in the quarter wavelength area of the vibrational wave output by the ultrasonic transducer 14 from the distal portion to the proximal side (area approximately over the entire length of the treatment portion 26a). The shape of the treatment portion 26a of the vibration transmitting member 26 may be formed as appropriate as long as easiness of treatment is secured as described below.

In a case in which treatment of the removal of liver tissue in a curved shape is to be conducted without using energy, when the distal portion 26a of the vibration transmitting member 26 is straight as described in the first and second embodiments, a single-time treatment area is in a straight shape. Thus, to conduct the treatment of the removal of the liver tissue in the curved shape, small straight-shaped treatment needs to be repeated while the direction of the distal portion 26a is changed. Conversely, since the treatment portion 26a of the vibration transmitting member 26 according to the present embodiment is bent in one direction, a single-time treatment area is approximately in an arc. Accordingly, the operation of repeating the small straight-shaped treatment can be omitted at the time of forming the treatment area in the curved shape. For this reason, when the liver tissue is to be dissected annularly, for example, existence of the bent portion 78 enables single treatment to be longer in length than the small straight-shaped treatment and to be conducted in a wider range. Accordingly, in a case in which the treatment portion 26a includes the bent portion 78, the number of times of opening/closing the clamp member 28 with respect to the treatment portion 26a can be decreased. That is, the number of times of movement of the vibration transmitting member 26 and the clamp member 28 and the number of times of turning of the clamp member 28 can be decreased. Also, due to the bent portion 78, at the time of forming the treatment area in the curved shape, it is possible to prevent excessive dissection of a dissected target such as liver tissue and to form a smoother treatment area.

Also, since the distal portion 26a of the vibration transmitting member 26 is bent, visibility of the clamp member 28 and the distal portion 26a of the vibration transmitting member 26 with use of a not-illustrated endoscope in laparoscopic surgery can be improved.

Next, a fourth embodiment will be described with reference to FIG. 6. The present embodiment is a modification example of the first to third embodiments. Members similar to or having similar functions to those described in the first to third embodiments are shown with the same reference numerals as much as possible, and detailed description of such similar components is omitted. In the present embodiment, the treatment portion 26a of the vibration transmitting member 26 may be straight as described in the first and second embodiments or bent as described in the third embodiment.

Figure 6:
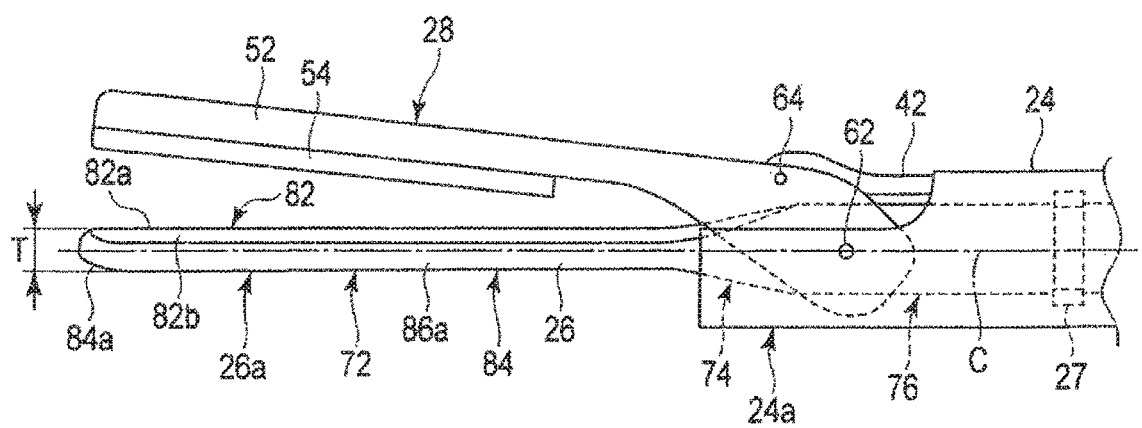
FIG. 6 illustrates a schematic side view of the part around the distal portion of the vibration transmitting member and the clamp member in the surgical apparatus of the surgical system according to the fourth embodiment.

As illustrated in FIG. 6, a distal end of the back surface 84 opposed to the treatment surface 82 in the treatment area 72 of the distal portion 26a of the vibration transmitting member 26 is provided with a cavitation generating surface 84a actively generating cavitation in an intended direction when vibration from the ultrasonic transducer 14 is transmitted to the distal end of the vibration transmitting member 26. The cavitation generating surface 84a is formed as a curved surface. The cavitation generating surface 84a generates the cavitation in a normal direction thereof when the vibration from the ultrasonic transducer 14 is transmitted to the distal end of the vibration transmitting member 26.

In this manner, the curved cavitation generating surface 84a is formed at the distal end of the back surface 84 in the treatment area 72 of the distal portion 26a of the vibration transmitting member 26. Thus, for example, the cavitation generating surface 84a can be brought into contact with liver tissue, and when the vibration from the ultrasonic transducer 14 is transmitted to the distal end of the vibration transmitting member 26, the liver tissue can be emulsified by the cavitation.

Next, a fifth embodiment will be described with reference to FIGS. 7A to 7C. The present embodiment is a modification example of the first to fourth embodiments. Members similar to or having similar functions to those described in the first to fourth embodiments are shown with the same reference numerals as much as possible, and detailed description of such similar components is omitted.

Figure 7A:
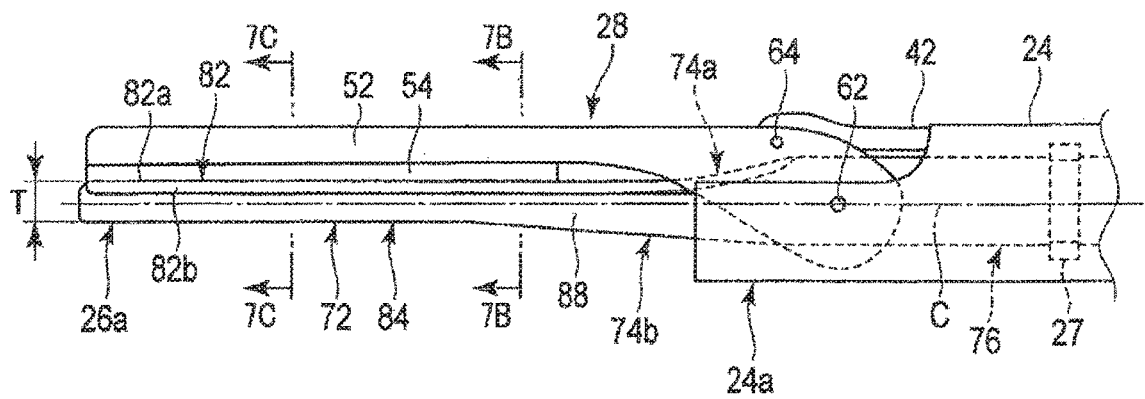
FIG. 7A illustrates a schematic side view of the part around the distal portion of the vibration transmitting member and the clamp member in the surgical apparatus of the surgical system according to the fifth embodiment.
Figure 7B:
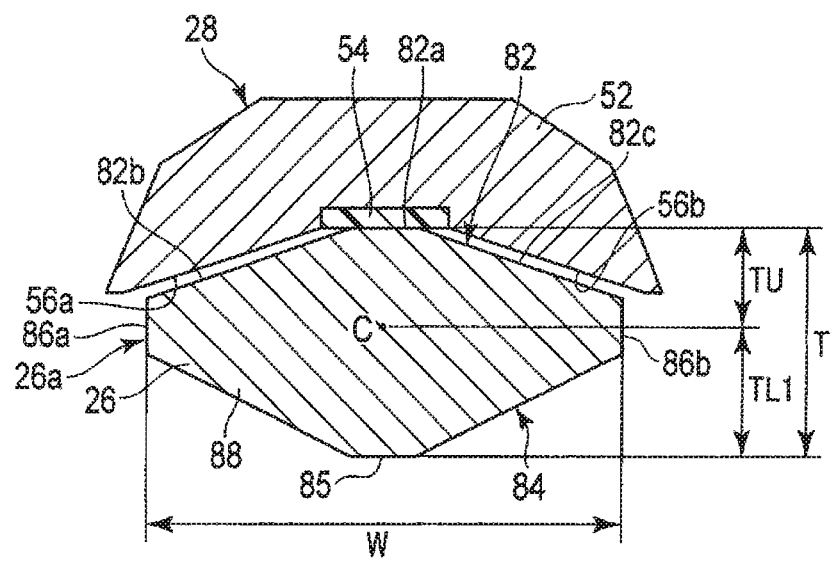
FIG. 7B illustrates a schematic horizontal cross-sectional view along line 7B-7B in FIG. 7A of the part around the distal portion of the vibration transmitting member and the clamp member in the surgical apparatus of the surgical system according to the fifth embodiment.
Figure 7C:
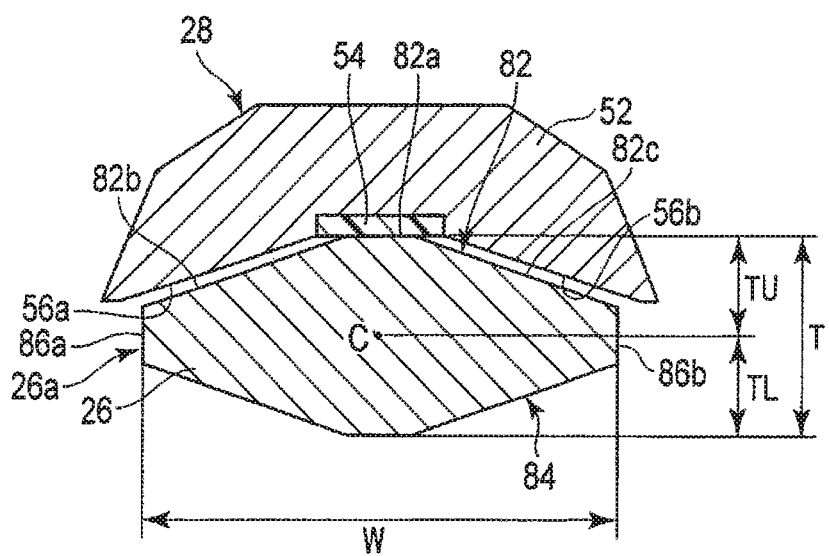
FIG. 7C illustrates a schematic horizontal cross-sectional view along line 7C-7C in FIG. 7A of the part around the distal portion of the vibration transmitting member and the clamp member in the surgical apparatus of the surgical system according to the fifth embodiment.

As illustrated in FIGS. 7A to 7C, when the clamp member 28 is closed with respect to the vibration transmitting member 26, the distal portion 26a of the vibration transmitting member 26 is supplied around a proximal end of the pressing pad 54 with highest stress. As illustrated in FIG. 7A, the middle area 74 of the treatment portion 26a of the vibration transmitting member 26 according to the present embodiment includes a short area 74a on the side of the treatment surface 82 and a long area 74b on the side of the back surface 84. The long area 74b on the side of the back surface 84 is longer than the short area 74a on the side of the treatment surface 82. Proximal positions of the short area 74a and the long area 74b along the center axis C are at equal or approximately equal positions, that is, at a position of a distal end of the rod-like area 76. The short area 74a is formed continuously to the treatment surface 82. The long area 74b is formed continuously to the back surface 84 on a proximal side of the back surface 84. Thus, the middle area 74 of the distal portion 26a of the vibration transmitting member 26 according to the present embodiment has an upper side and a lower side asymmetric across the longitudinal axis C in FIG. 7A and forms a longer thick part than the middle area 74 of the distal portion 26a of the vibration transmitting member 26 described in the first to fourth embodiments. That is, the treatment area 72 according to the present embodiment includes not only a parallel part to the center axis C but also a part of a thick portion 88.

Here, as illustrated in FIGS. 7A and 7B, in the middle area 74, the distance TU from the center axis C to the top portion (dissecting area) 82a of the treatment surface 82 is shorter than a distance TL1 from the center axis C to a top portion 85 of the back surface 84. Thus, the long area 74b of the middle area 74 is provided with the thick portion 88, which is thicker than the short area 74a. That is, the long area 74b of the middle area 74 includes the thick portion 88. Meanwhile, as illustrated in FIGS. 7A and 7C, in the treatment area 72, the distance TU from the center axis C to the top portion (dissecting area) 82a of the treatment surface 82 is approximately equal to the distance TL from the center axis C to the top portion 85 of the back surface 84. Meanwhile, the top portion (dissecting area) 82a of the treatment surface 82 is an abutting surface on which the pressing pad 54 is to abut.

Consequently, in the present embodiment, the treatment area (parallel area) 72 provided to be parallel to or approximately parallel to the center axis C and adapted to conduct treatment to living tissue is shorter on the back surface 84 than those described in the first to fourth embodiments. On the other hand, the treatment area (parallel area) 72 provided to be parallel to or approximately parallel to the center axis C and adapted to conduct treatment to living tissue can be formed on the treatment surface 82 to be similar to those described in the first to fourth embodiments. That is, the thick portion 88 of the back surface 84 has a part which is not parallel to the longitudinal axis C. As a matter of course, a part of the back surface 84 located further on the distal side than the thick portion 88 can be parallel to the longitudinal axis C.

In this manner, the thick portion 88 is formed on the back surface 84 on the opposite side of the treatment surface 82 with the longitudinal axis C, extended from the proximal portion to the distal portion around an abutting part on which the proximal end of the pressing pad 54 along the longitudinal axis C in the dissecting area 82a abuts, interposed therebetween. The thick portion 88 is thicker than the part continued to the treatment surface 82 with the longitudinal axis C interposed therebetween from the distal side toward the proximal side along the longitudinal axis C. Also, in a state in which the proximal end of the pressing pad 54 of the clamp member 28 abuts on the dissecting area 82a, the proximal end of the pressing pad 54 of the clamp member 28 is located between a distal end and a proximal end of the thick portion 88 along the longitudinal axis C. That is, the thick portion 88 is formed to be gradually thicker along the longitudinal axis C from a part in the dissecting area 82a further on the distal side than the proximal position of the pressing pad 54 along the longitudinal axis C toward a part further on the proximal side than the proximal position.

Thus, due to the thick portion 88, the distal portion 26a of the vibration transmitting member 26 according to the present embodiment, especially the proximal end of the pressing pad 54, can improve resistance to stress more than the distal portion 26a of the vibration transmitting member 26 described in the first to fourth embodiments. Consequently, the amount of deformation of the treatment area 72 of the distal portion 26a of the vibration transmitting member 26 can be restricted. Thus, according to the present embodiment, it is possible to provide the vibration transmitting member 26 and the surgical apparatus 12 enabling resistance to stress in grasping to be secured without influencing treatment performance even in a case of proceeding with size reduction (diameter reduction) of the vibration transmitting member 26 and to restrict to the minimum changes in center of gravity on respective vertical cross-sectional surfaces to the longitudinal axis C and vibration destabilizing elements resulting from the discontinuous changes.

Meanwhile, the bent portion 78 described in the fourth embodiment can be formed at an appropriate position although it is not illustrated. That is, for example, the bent portion 78 may be formed at a part including the thick portion 88, at the treatment area 72, or at both the parts.

Several embodiments have specifically been described above with reference to the drawings. However, the present invention is not limited to the aforementioned embodiments but includes every embodiment carried out without departing from the spirit and scope thereof.

What is claimed is:

1. A vibration transmitting member for use with a clamp member, the vibration transmitting member being configured to transmit vibration from an ultrasonic transducer, the vibration transmitting member comprising:
   a body having a distal portion with a first surface, an opposite surface, and first and second side surfaces extending between the first surface and the opposite surface, the body further having a proximal portion;
   wherein:
   the body extending along a longitudinal axis extending from the proximal portion toward the distal portion,
   the first surface configured to face the clamp member, the first surface having a ridge extending along the longitudinal axis,
   the ridge configured to extend toward the clamp member in a thickness direction of the distal portion more than other portions of the first surface,
   the opposite surface configured to oppose the first surface, the opposite surface having a projection extending along the longitudinal axis,
   the projection configured to protrude more than other portions of the opposite surface in the thickness direction, and
   a maximum thickness of the distal portion through the ridge and the projection in the thickness direction is smaller than a maximum width of the distal portion in a width direction perpendicular to the thickness direction,
   the distal portion having a first portion with a first maximum width between the first and second side surfaces in the width direction, a second portion with a second maximum width between the first and second side surfaces in the width direction, and a tapered transition portion between the first portion and the second portion,
   the first portion having a distal end of the body,
   the second portion arranged proximal to the first portion, and
   the first maximum width being larger than the second maximum width, and
   the first and second side surfaces having portions in the second portion which are parallel with each other along the longitudinal axis, the portions defining the second maximum width.

2. The vibration transmitting member according to claim 1, wherein the distal portion comprises a cavitation generating surface which is provided on a back surface of the distal portion opposite to the first surface and which is formed as a curved surface, the cavitation generating surface configured to generate cavitation when the vibration is transmitted thereto.

3. The vibration transmitting member according to claim 1, wherein the distal portion comprises a treatment area and a middle area proximal to the treatment area, wherein a bent portion is formed between a distal end of the treatment area and a distal end of the middle area.

4. The vibration transmitting member according to claim 1 further comprising an intermediate portion between the distal portion and the proximal portion, the intermediate portion is configured such that a first maximum thickness between the first surface and the longitudinal axis in the thickness direction is smaller than a second maximum thickness between the opposite surface and the longitudinal axis in the thickness direction.

5. A surgical apparatus comprising:
   the vibration transmitting member according to claim 1; and
   the clamp member, wherein the clamp member is configured to approach to and separate from the vibration transmitting member.

6. The surgical apparatus according to claim 5, wherein the clamp member includes:
   an electrode having electrical conductivity, and
   a pad having electrical insulation which is adjacent to the electrode,
   the ridge is a dissecting area transmitting ultrasonic vibration thereto to enable dissection of living tissue,
   the first surface comprises sealing areas having electrical conductivity which are configured to extend from the dissecting area in the width direction and enable coagulation and sealing of the living tissue by electric conduction between the sealing areas and the electrode of the clamp member, and
   the dissecting area is configured to contact with the pad, and the sealing areas are separated from the electrode when the clamp member approaches to the vibration transmitting member.

7. The vibration transmitting member according to claim 1, wherein
   the distal portion includes a treatment area adapted to conduct treatment, a middle area formed on a proximal side of the treatment area, and a rod-like area formed on a proximal side of the middle area, and
   a distance at the treatment area between the longitudinal axis and the opposite surface is smaller than a distance at the middle area between the longitudinal axis and the opposite surface in the thickness direction.

8. The vibration transmitting member according to claim 7, wherein a distance between the longitudinal axis and the first surface is smaller than a distance between the longitudinal axis and the opposite surface in the thickness direction, at the middle area.

* * * * *